(12) United States Patent
Nekouzadeh et al.

(10) Patent No.: US 12,290,666 B2
(45) Date of Patent: May 6, 2025

(54) DRUG DELIVERY DEVICES WITH PARTIAL NEEDLE RETRACTION

(71) Applicant: AMGEN INC., Thousand Oaks, CA (US)

(72) Inventors: Ali Nekouzadeh, Simi Valley, CA (US); Carl Conrath, Thousand Oaks, CA (US); Basel Hasan Taha, Simi Valley, CA (US)

(73) Assignee: AMGEN INC., Thousand Oaks, CA (US)

( * ) Notice: Subject to any disclaimer, the term of this patent is extended or adjusted under 35 U.S.C. 154(b) by 971 days.

(21) Appl. No.: 17/277,555

(22) PCT Filed: Oct. 22, 2019

(86) PCT No.: PCT/US2019/057370
§ 371 (c)(1),
(2) Date: Mar. 18, 2021

(87) PCT Pub. No.: WO2020/092056
PCT Pub. Date: May 7, 2020

(65) Prior Publication Data
US 2022/0031953 A1      Feb. 3, 2022

Related U.S. Application Data

(60) Provisional application No. 62/754,362, filed on Nov. 1, 2018.

(51) Int. Cl.
*A61M 5/315* (2006.01)
*A61M 5/20* (2006.01)

(52) U.S. Cl.
CPC ...... *A61M 5/31511* (2013.01); *A61M 5/2033* (2013.01); *A61M 5/31501* (2013.01)

(58) Field of Classification Search
CPC ............ A61M 5/31511; A61M 5/2033; A61M 5/31501; A61M 5/20
See application file for complete search history.

(56) References Cited

U.S. PATENT DOCUMENTS 3,316,909 A    5/1967  Cowley
3,720,211 A    3/1973  Kyrias
(Continued)

FOREIGN PATENT DOCUMENTS

CN     103249443 B    10/2015
GB       2550924 A    12/2017
(Continued)

OTHER PUBLICATIONS

International Search Report and Written Opinion for International Patent Application No. PCT/US2019/055010, dated Jan. 20, 2020.
(Continued)

*Primary Examiner* — Theodore J Stigell
(74) *Attorney, Agent, or Firm* — MARSHALL, GERSTEIN & BORUN LLP (57) ABSTRACT

Methods, devices, and components are provided to reduce tissue resistive pressure during a subcutaneous drug delivery operation by increasing the size of the injection cavity by partially retracting the drug delivery member after inserting the drug delivery member to a subcutaneous position. The drug delivery devices described herein include a resilient member that interacts between stationary and moveable components of the drug delivery device. The drug delivery device include drives to move the stationary and moveable components relative to one another to insert a drug delivery member to a subcutaneous depth within a patient and to dispense a drug to the injection cavity in the patient. The resilient member is deformed during the operations or is pre-deformed and the stored energy of the resilient member in the deformed state then acts on the stationary and move- (Continued)

able components to partially retract the drug delivery member to relieve pressure in the injection region.

12 Claims, 5 Drawing Sheets

(56) References Cited

U.S. PATENT DOCUMENTS

| | | | |
|---|---|---|---|
| 3,797,489 | A | 3/1974 | Sarnoff |
| 4,699,612 | A | 10/1987 | Hamacher |
| 6,478,768 | B1 | 11/2002 | Kneer |
| 8,795,230 | B2 | 8/2014 | Schoonmaker et al. |
| 9,814,840 | B2 | 11/2017 | Cowe et al. |
| 9,844,635 | B2 | 12/2017 | Schoonmaker et al. |
| 9,849,252 | B2 | 12/2017 | Armes |
| 2010/0076400 | A1 | 3/2010 | Wall |
| 2015/0174326 | A1 | 6/2015 | Bokelman et al. |
| 2016/0128576 | A1 | 5/2016 | Chiang et al. |
| 2016/0256106 | A1 | 9/2016 | Krasnow et al. |
| 2016/0302868 | A1 | 10/2016 | Nagale et al. |
| 2017/0106146 | A1* | 4/2017 | Folk ................ A61M 5/20 |
| 2017/0216526 | A1 | 8/2017 | Brereton et al. |
| 2018/0021508 | A1 | 1/2018 | Destefano et al. |

FOREIGN PATENT DOCUMENTS

| | | |
|---|---|---|
| KR | 101776258 B1 | 9/2017 |
| TW | 201315499 A | 4/2013 |
| WO | WO-2012/045831 A1 | 4/2012 |
| WO | WO-2013028906 A1 | 2/2013 |
| WO | WO-2014/150201 A1 | 9/2014 |
| WO | WO-2015/171777 A1 | 11/2015 |
| WO | WO-2016/003813 A1 | 1/2016 |
| WO | WO-2018/055433 A1 | 3/2018 |
| WO | WO-2018/136398 A1 | 7/2018 |
| WO | WO-2019/081947 A1 | 5/2019 |

OTHER PUBLICATIONS

International Application No. PCT/US2019/057370, International Search Report and Written Opinion, mailed Jan. 27, 2020.
International Application No. PCT/US2019/056073, International Search Report and Written Opinion, mailed Feb. 3, 2020.

* cited by examiner

DRUG DELIVERY DEVICES WITH PARTIAL NEEDLE RETRACTION

CROSS-REFERENCE TO RELATED APPLICATIONS

This is the United States national phase of International Patent Application No. PCT/US19/57370, filed Oct. 22, 2019, which application claims priority to U.S. Provisional Patent Application No. 62/754,362, filed Nov. 1, 2018, the entire contents of each of which are hereby incorporated by reference herein.

FIELD OF DISCLOSURE

The present disclosure generally relates to drug delivery devices and, more particularly, to needle insertion mechanisms for drug delivery devices.

BACKGROUND

Drugs can be administered through the use of drug delivery devices such as autoinjectors or on-body injectors (also referred to as wearable injectors). Autoinjectors and on-body injectors may be used to help automate the injection and delivery or administration process, thereby simplifying the process for certain patient groups or sub-groups for which use of the syringe/vial combination or pre-filled syringe systems would be disadvantageous, whether because of physiological or psychological impediments.

Subcutaneous injection is one method for a gradual release of drug product into the blood stream and is the injection type in most autoinjector and on-body injector drug delivery devices. The limited amount of blood vessels and fluid paths within the subcutaneous tissue, however, can cause a pressure build up at the point of injection. This pressure can resist the injection, can cause significant variability in the injection time, and may cause pain for the patients.

SUMMARY

In accordance with a first aspect, a drug delivery device is described that includes an outer casing having one or more sidewalls, a distal end wall with an opening extending therethrough, and a proximal end wall defining an interior. The drug delivery device further includes a primary container assembly that is at least partially received within the interior of the outer casing. The primary container assembly includes a reservoir having a sidewall defining an interior, a plunger stopper disposed within the interior of the reservoir, and a drug delivery member secured to the reservoir to be fluidly coupled to the interior thereof, at least the drug delivery member being movable between first and second positions with respect to the outer casing. A resilient member is disposed between the primary container assembly and the outer casing, such that the resilient member is in a deformed state with the drug delivery member in the second position and biases the drug delivery member to move in a retraction direction toward the first position to partially retract the drug delivery member to a retracted position.

According to some versions, the primary container assembly includes a distal end, which can be a distal end of the reservoir or a distal end of a housing at least partially receiving the reservoir and drug delivery member therein, and the resilient member is disposed between the distal end of the primary container assembly and the distal end wall of the outer casing.

According to some versions, the primary container assembly includes an outwardly projecting flange at a proximal end thereof opposite the drug delivery member and the outer casing includes an inwardly projecting flange. In these versions, the resilient member can be disposed between the outwardly and inwardly projecting flanges. In one form, the proximal end of the primary container assembly can be a proximal end of the reservoir. In another form, the primary container assembly further includes a housing that at least partially receives the reservoir and drug delivery member therein and the proximal end of the primary container assembly is a proximal end of the housing.

In further approaches, the drug delivery device can include a drive mechanism that is configured to drive movement of the primary container assembly with respect to the outer casing in a first direction from the first position to the second position such that the drug delivery member extends through the opening in the distal end wall of the outer casing for a drug delivery member insertion operation. If desired, the drive mechanism can include a drive rod and the drive mechanism can be configured to drive the plunger rod to drive movement of the plunger stopper through the reservoir to expel a drug through the drug delivery member during a drug delivery operation. In these forms, the plunger stopper being driven through the reservoir can cause the resilient member to deform and bias the primary container assembly to move in the second, opposite direction with respect to the outer casing to partially retract the drug delivery member after the drug delivery operation. The forms can further include a releasable catch that is configured to hold the resilient member in the deformed state after at least one of the drug delivery member insertion or drug dispensing operation.

The above drug delivery devices can also include one or more of the following aspects: the resilient member can be a spring or an elastomeric bumper; the resilient member can be one or more cantilevered tabs that extend inwardly from the one or more sidewalls of the outer casing with inward end portions that disposed within a path of the primary container assembly; the drug delivery device can include a release member that engages primary container assembly or both the primary container assembly and the resilient member and holds the resilient member in the deformed state; or the drug delivery device can include a locking mechanism having a lock member that is deflectable by the primary container assembly as the primary container assembly is moved in the retraction direction and a biasing mechanism that is configured to bias the lock member into a path of a portion of the primary container assembly in the insertion direction to restrict further movement of the primary container assembly.

In accordance with a second aspect, a method for operating a drug delivery device having any of the above configurations is disclosed that includes deforming a resilient member disposed between the primary container assembly and the outer casing due to the movement of the drug delivery member with respect to the outer casing during the drug delivery member insertion operation, and biasing the drug delivery member with the resilient member to move in a second, opposite direction with respect to the outer casing to partially retract the drug delivery member after the drug delivery member insertion operation.

According to some versions, deforming the resilient member disposed between the primary container assembly and the outer casing can include deforming the resilient member disposed between a distal end of the primary container assembly and the distal end wall of the outer casing. According to a further form, deforming the resilient member disposed between the distal end of the primary container assembly and the distal end wall of the outer casing can be one of: deforming the resilient member disposed between a distal end of the primary container assembly and the distal end wall of the outer casing a distal end of the reservoir or deforming the resilient member disposed between a distal end of a housing of the primary container assembly at least partially receiving the reservoir and drug delivery member therein and the distal end wall of the outer casing.

According to some versions, the primary container assembly can include an outwardly projecting flange at a proximal end thereof opposite the drug delivery member and the outer casing can include an inwardly projecting flange. In these versions, deforming the resilient member disposed between portions of the primary container assembly and the outer casing can include deforming the resilient member disposed between the outwardly and inwardly projecting flanges.

The above versions can further include one or more of the following aspects: deforming the resilient member can include compressing a spring or an elastomeric bumper; deforming the resilient member can include deflecting one or more cantilevered tabs extending inwardly from the one or more sidewalls of the outer casing with portions disposed within a path of the primary container assembly; the method can include driving movement of the primary container assembly with respect to the outer casing in an insertion direction with a drive mechanism of the drug delivery device such that the drug delivery member extends through the opening in the distal end wall of the outer casing for a drug delivery member insertion operation; the method can include driving a plunger rod to drive movement of the plunger stopper through the reservoir to expel a drug through the drug delivery member during a drug delivery operation, deforming the resilient member disposed between the portions of the primary container assembly and the outer casing due to movement of the primary container assembly with respect to the outer casing during the drug delivery operation, and biasing the primary container assembly with the resilient member to move in the second, opposite direction with respect to the outer casing to partially retract the drug delivery member after the drug delivery operation; or the method can include holding the resilient member in the deformed state with a releasable catch and biasing the drug delivery member with the resilient member to move in the second, opposite direction with respect to the outer casing to partially retract the drug delivery member can include releasing the releasable catch.

BRIEF DESCRIPTION OF THE DRAWINGS

The above needs are at least partially met through provision of the embodiments described in the following detailed description, particularly when studied in conjunction with the drawings, wherein.

DETAILED DESCRIPTION

Methods, devices, and components are provided to reduce tissue resistive pressure during a subcutaneous drug delivery operation by increasing the size of the injection cavity by partially retracting the drug delivery member after inserting the drug delivery member to a subcutaneous position. An injection cavity refers to cavity at the tip of the needle inside of the patient. The drug delivery devices described herein include a resilient member, such as a spring or an elastic/viscoelastic material, that interacts between stationary and moveable components of the drug delivery device. The drug delivery device include drives to move the stationary and moveable components relative to one another to insert a drug delivery member to a subcutaneous depth within a patient and to dispense a drug to the injection cavity in the patient. The resilient member undergoes any form of deformation, including compression, deflection, stretching, twisting, etc., during the drug delivery member insertion and/or drug delivery operations and the stored energy of the resilient member in the deformed state then acts on the stationary and moveable components to partially retract the drug delivery member to relieve pressure in the injection cavity. In some versions, the resilient member can be pre-deformed and kept in the deformed state with a catch release mechanism. The resilient member may be released from the deformed state automatically or manually during any stage of the injection, such as after the drug delivery member insertion operation and/or during the drug dispensing operation, to initiate the partial retraction of the drug delivery member. The resilient member and drive mechanism may be designed so that partial drug delivery member retraction occurs gradually after the automatic or manual drug delivery member insertion for a predetermined amount of time or to the end of injection, or may be designed so that the partial drug delivery member retraction occurs partly after automatic or manual drug delivery member insertion and partly throughout the drug dispensing operation.

Figure 1:
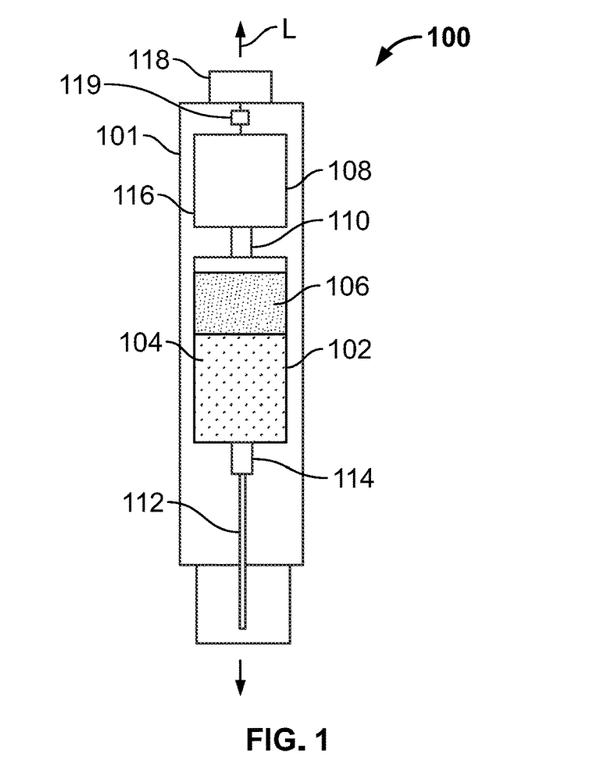
FIG. 1 is a diagrammatic view of an autoinjector drug delivery device in accordance with various embodiments.

In some versions as illustrated in FIG. 1, drug delivery devices 100, such as autoinjectors, can have a vertically oriented configuration with some or all drug delivery components disposed in stacked relation along a longitudinal axis L within a housing 101 of the devices 100. More specifically, the devices 100 can be configured to operate and inject a user with the device 100 oriented generally perpendicular to a skin surface of the user. The drug delivery components can include a reservoir 102 having a drug 104 contained therein, a plunger stopper 106 disposed within the reservoir 102 and sildably movable therein along the longitudinal axis L, a drive mechanism 108 coupled to a plunger rod 110 to drive the plunger stopper 106 through the reservoir 102, a drug delivery member 112 oriented along the longitudinal axis L, a flow path or hub 114 fluidly coupling the reservoir 102 to the drug delivery member 112, and a needle insertion mechanism 116 configured to insert the drug delivery member 112 to a desired subcutaneous depth within the user. In one version of the depicted drug delivery device 100 of FIG. 1, the drug delivery member 112 can include a rigid hollow needle, conventionally used with syringes and/or auto-injectors.

By some approaches, the needle insertion mechanism 116 can be a drive mechanism to longitudinally move the needle a desired distance. Suitable drive mechanisms include, but are not limited to, springs, gas sources, phase changing materials, motors, or other electromechanical systems. Pursuant to this, the device 100 can include electronic components, such as a controller 119, to control operation of one or more of the drug delivery components. Example autoinjector devices are described in U.S. Ser. No. 62/447,174, filed Jan. 17, 2017, which is hereby incorporated by reference herein. If desired, the drive mechanisms 108, 116 can be a single mechanism configured to drive both movement of the plunger stopper 106 and the drug delivery member 112 by moving some or all of the reservoir 102, hub 114, and drug delivery member 112. As commonly configured, one or more of the components of the device 100, such as the drive mechanism 108 and needle insertion mechanism 116, can be operable in response to actuation of a user input device 118 accessible on an exterior of the housing 101. In other versions, including those described below with reference to FIGS. 7 and 8, the drug delivery member 112 may be inserted manually, including with the use of a needle guard.

Figure 2:
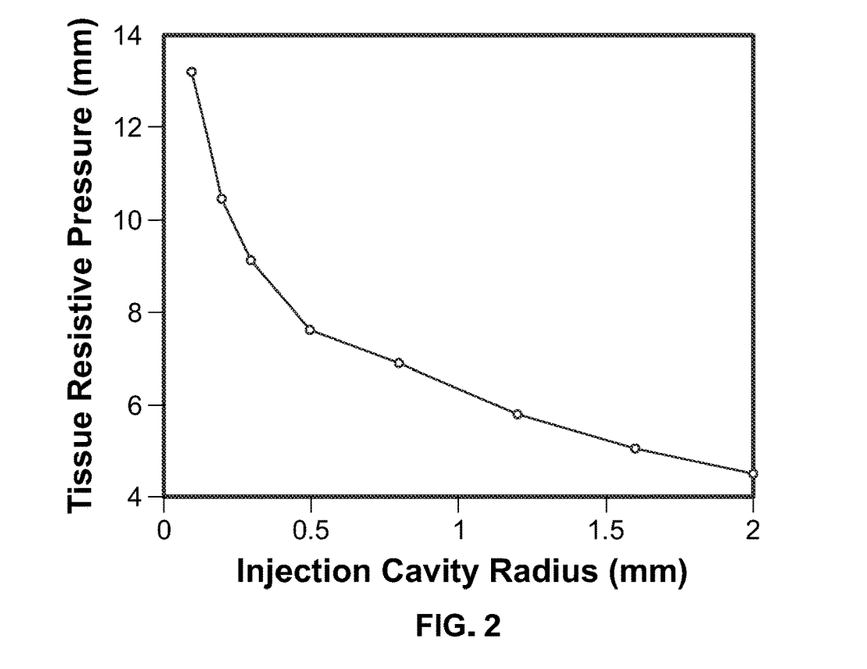
FIG. 2 is a graph showing simulation results for the variation of steady state tissue resistive pressure as a function of the injection cavity radius.

It has been found through simulations based on a developed de novo model of the flow of drug product within the subcutaneous tissue, that the magnitude of the tissue resistive pressure, in addition to drug product viscosity and injection rate, depends on the volume of the injection cavity at the point of injection. Simulation results for the variation of the steady state tissue resistive pressure as a function of the injection cavity radius is shown in FIG. 2. The simulation utilized a drug product viscosity of 10 cP and an injection rate of 6.0 mL/min. The horizontal axis is the diameter of the injection cavity in mm and the vertical axis is the tissue resistive pressure in psi. As shown, the simulation results demonstrate that increasing the size of the injection cavity reduces the tissue resistive pressure against the injection. Further, it is believed that partial retraction of the needle, following insertion to a subcutaneous position, is a viable mechanism to increase the size of the injection cavity and therefore to reduce the tissue resistive pressure.

Example mechanisms for implementing a partial needle retraction to reduce the tissue resistive pressure are shown in FIGS. 3-8. In each of the examples of FIGS. 3-6, an autoinjector 200 is shown in a diagrammatic form for simplicity and ease of showing interacting components configured to cause the needle retraction. Each autoinjector 200 includes an outer casing 202 including one or more sidewalls 204, a proximal end wall 206, and a distal end wall 208 defining an interior 210 sized to receive a primary container assembly 212 therein. In the depicted version, the primary container assembly 212 can include a syringe assembly. The casing 202 and one or more components of the primary container assembly 212 are movable with respect to one another to perform an injection operation.

Each of the example autoinjectors 200 further include a resilient member 214 configured to bias portions of the casing 202 and the primary container assembly 212 away from each other after an initial insertion operation and during a drug dispensing operation to relieve pressure within the injection area of the patient.

As shown in FIGS. 3-8, the primary container assembly 212 includes a reservoir 216 containing a drug 218 in an interior 220 thereof, a plunger stopper 222 received within the reservoir interior 220 adjacent to a proximal end 224 thereof, and a drug delivery member including a needle 226 mounted to a distal end 228 of the reservoir 216 to fluidly couple the needle 226 to the reservoir interior 220. For example, the needle 226 can be mounted within a hub 230 of the reservoir 216. Further, if desired, the primary container assembly 212 can include an outer housing 231 encasing the reservoir 216. For example, the outer housing 231 can be an cassette configured to be inserted and removed from the outer casing 202.

As with the above embodiment, the autoinjector 200 of this form further includes a drive assembly 232 to drive movement of one of the casing 202 and the primary container assembly 212 with respect to one another so that the needle 226 is driven through an opening 233 in the distal end wall 208 of the casing 202 to insert the needle 226 to an injection depth within a patient. In the illustrated form, the drive assembly 232 includes a drive mechanism 234 and a drive rod or piston 236. The drive mechanism 234 can be a spring, as shown, or other suitable mechanisms, such as gas sources, phase changing materials, motors, or other electromechanical systems. Upon actuation of the autoinjector 200, e.g., in response to actuation the user input 118, the drive mechanism 234 is released or activated to drive movement of the primary container assembly 212 relative to the casing 202 in a first, insertion direction. As discussed above, when the needle 226 is inserted to the injection depth and the injection started, pressure can build up around a tip 238 of the needle 226, which can undesirably resist the injection, cause variability in the injection time, and cause pain for the patient. Advantageously, movement of the primary container assembly 212 within the casing 202 compresses or deflects the resilient member 214, such that after the drive mechanism 234 inserts the needle 226 to a predetermined depth, the resilient member 214 at least partially returns to an original configuration to move portions of the primary container assembly 212 and casing 202 away from one another causing the tip 238 of the needle 226 to slightly retract within the patient in a second, retraction direction. This retraction action relieves pressure in the injection cavity in the patient.

After the needle 226 is inserted to a desired depth, the drive mechanism 234 drives movement of the rod 236 to engage the plunger stopper 222 and drive the plunger stopper 222 through the reservoir 216 to expel the drug 218 through the needle 226 and into the patient. This drug dispensing operation again compresses or deflects the resilient member 214 due to the fluid-solid interaction between the plunger stopper 222, the reservoir 216, and the drug being dispensed increasing the pressure of the drug, as well as the plunger stopper 222 frictionally engaging a sidewall 240 of the reservoir 216 as the plunger stopper 222 is driven therethough. As the injection progresses, the force of the drive mechanism 234 decreases as the plunger stopper 222 approaches the distal end 228 of the reservoir 216. So configured, the resilient member 214 sequentially returns toward an uncompressed or undeflected state during the drug dispensing operation. The drive mechanism 234 can include separate drives for the needle insertion and drug dispensing operations, which can take any of the forms described above.

Figure 3:
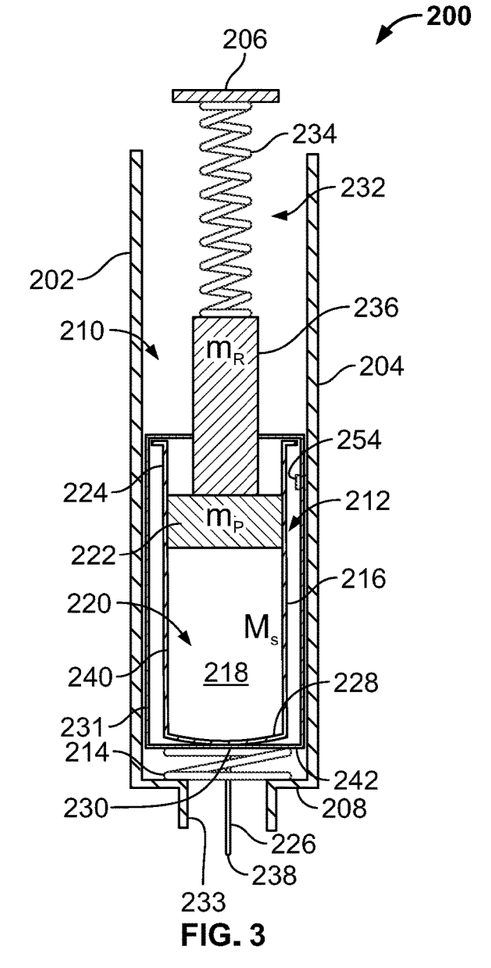
FIG. 3 is a diagrammatic view of a first example drug delivery device configured to cause partial drug delivery member retraction in accordance with various embodiments.
Figure 4:
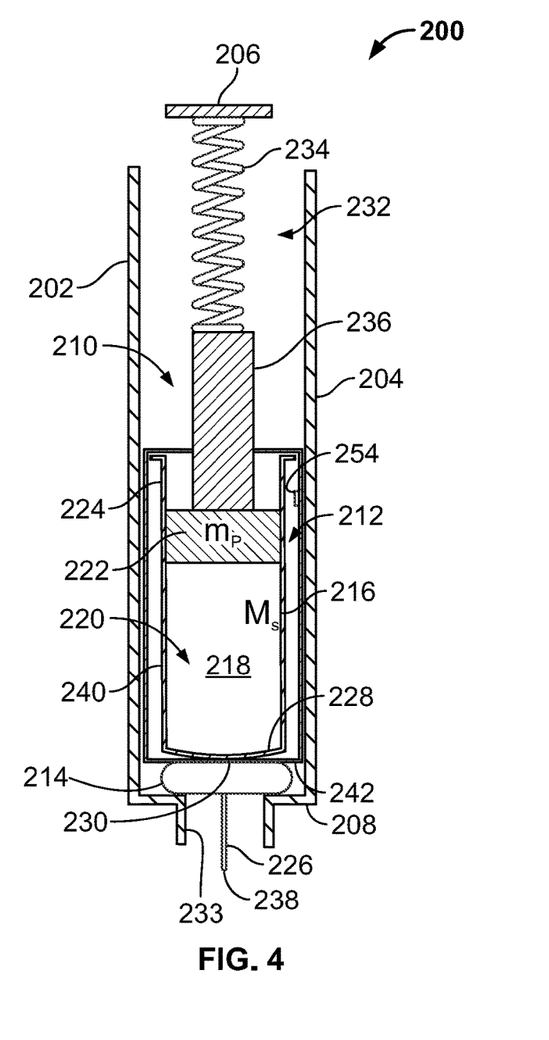
FIG. 4 is a diagrammatic view of a second example drug delivery device configured to cause partial drug delivery member retraction in accordance with various embodiments.
Figure 5:
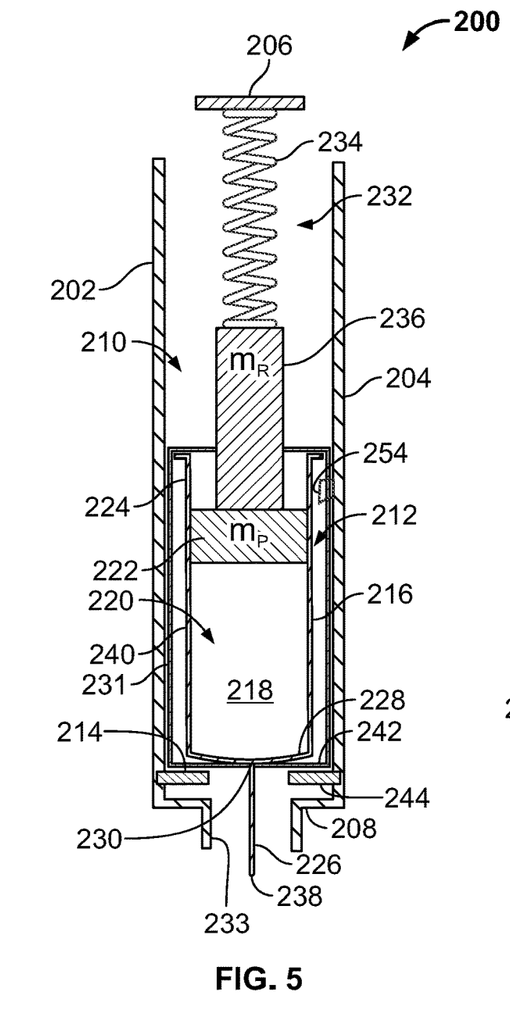
FIG. 5 is a diagrammatic view of a third example drug delivery device configured to cause partial drug delivery member retraction in accordance with various embodiments.

The resilient member 214 can be positioned within the autoinjector in a number of suitable configurations. In a first example as shown in FIG. 3, the resilient member 214 is a compression spring disposed between the distal end wall 208 of the outer casing 202 and a distal end of the primary container assembly 212. In some versions, the compression spring is disposed adjacent to the distal end 228 of the reservoir 216 and, in other versions, the compression spring is disposed adjacent to a distal end 242 of the housing 231. The springs described herein can be formed from any suitable material, including metals, elastic, or viscoelastic materials. In a second example as shown in FIG. 4, the resilient member 214 is an elastomeric bumper disposed between the distal end wall 208 of the outer casing 202 and a distal end of the primary container assembly 212. In some versions, the elastomer bumper is disposed adjacent to the distal end 228 of the reservoir 216 and in other versions the elastomeric bumper is disposed adjacent to the distal end 242 of the housing 231. The elastomeric bumper can be a ring as shown, other closed shapes, or discrete members secured to one of the primary container assembly 212 or outer casing 202. In a third example as shown in FIG. 5, the resilient member 214 is one or more cantilevers that project inwardly from the casing sidewall 204. Inward edge portions 244 of the cantilevers are disposed within a longitudinal path of the primary container assembly 212 and, as such, the distal end 228 of the reservoir 216 or distal end 242 of the housing 231 resiliently deflects the cantilevers during the insertion and drug delivery operations. Thereafter, the cantilevers bias the primary container assembly 212 away from the patient to partially retract the needle 226. The resilient member 214 can be secured to one or both the outer casing 202 and primary container assembly 212 by any suitable mechanism, including adhesive, fasteners, clamps, and so forth.

In alternative versions, the reservoir 216 or housing 231 can include a proximal flange 246 that projects outwardly therefrom and the outer casing 202 can include an inwardly projecting flange 250 disposed forwardly of the proximal flange 246 to define an area 252 therebetween to receive the resilient member 214. So configured, when the primary container assembly 212 moves relative to the outer casing 202, the resilient member 214 compresses and biases the components away from one another to achieve partial needle retraction. In the illustrated form, the resilient member 214 is a compression spring with ends captured between the flanges 246, 250. In other versions, the resilient member 214 can be an elastomeric bumper or one of the flanges 246, 250 can be a resilient cantilever similar to the above embodiments.

Figure 6:
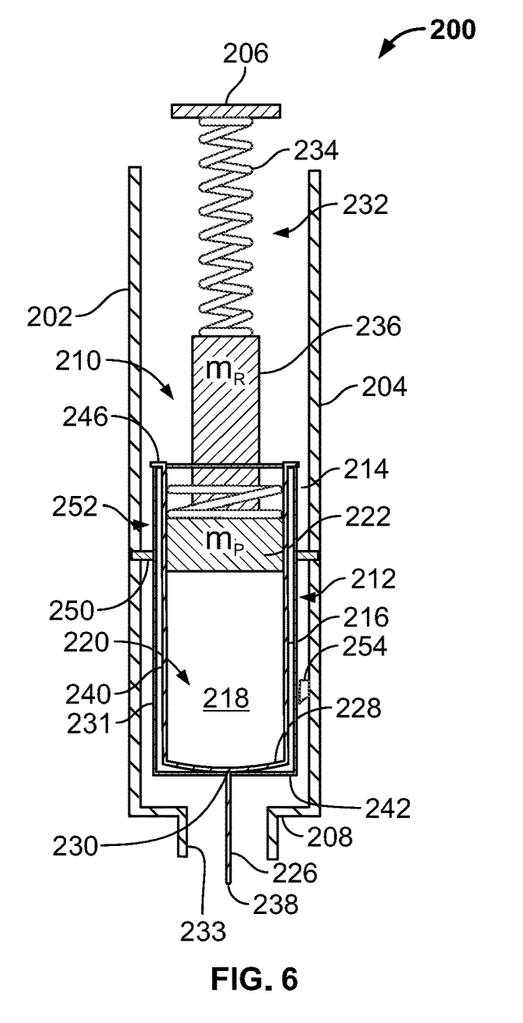
FIG. 6 is a diagrammatic view of a fourth example drug delivery device configured to cause partial drug delivery member retraction in accordance with various embodiments.

In further versions, as shown in FIG. 6, the resilient member 214 can be a tension spring or elastic material and can be coupled between the proximal end 224 of the reservoir 216 and the proximal end wall 206 to be extended during the needle insertion and drug delivery operations to thereby pull the components together to cause partial needle retraction. Other versions can resiliently twist the resilient member 214.

If desired, any of the above forms of the autoinjector 200 can include a catch and release mechanism 254 to hold the resilient member 214 in the compressed or deflected state after the needle insertion and/or drug delivery operation and a user can manipulate the mechanism 254 to release the resilient member 214 and cause the partial retraction of the needle 226.

Figure 7:
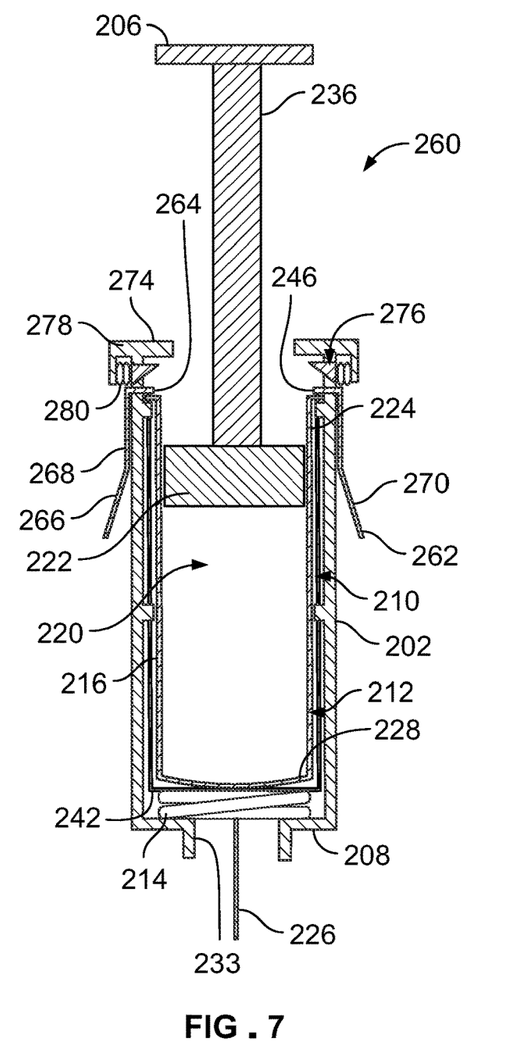
FIG. 7 is a diagrammatic view of a fifth example drug delivery device configured to cause partial drug delivery member retraction in accordance with various embodiments.
Figure 8:
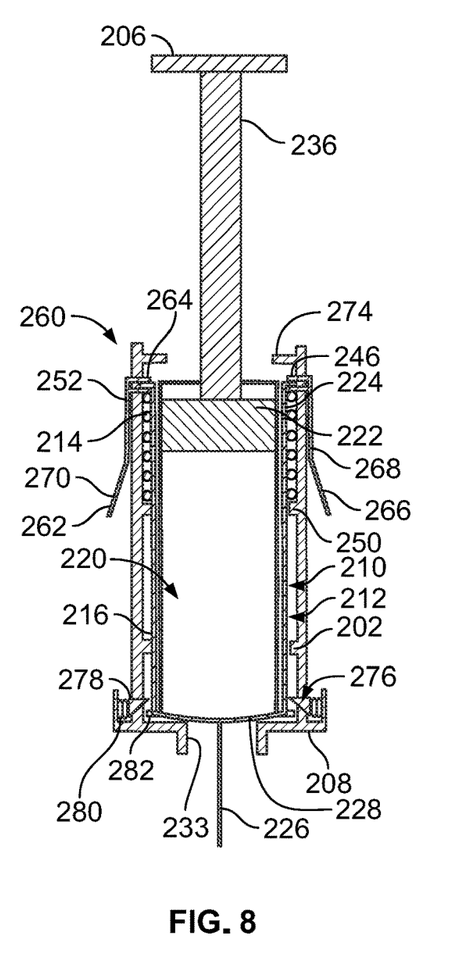
FIG. 8 is a diagrammatic view of a sixth example drug delivery device configured to cause partial drug delivery member retraction in accordance with various embodiments.

As shown in FIGS. 7 and 8, a partial needle retraction assembly 260 may be implemented so that the patient can trigger a partial needle retraction as desired to facilitate the injection, if necessary. The resilient member 214 can be disposed between the distal end wall 208 of the outer casing 202 and a distal end, 228, 242 of the primary container assembly 212 or in the area 252 between the flanges 246, 250. Although the retraction assembly 260 is shown with a spring 214, any of the resilient members described herein could alternatively be utilized. Moreover, the assembly 260 is shown with manual needle insertion and plunger operation. Of course, however, the assembly 260 can also be utilized in any of the above forms utilizing the drive 234. Specifically, the assembly 260 can be utilized in both automatic needle insertion and manual needle insertion, which can include a retracting needle guard, and can be implemented in automatic injection systems, as well as injection assistor devices.

The assembly 260 includes a release mechanism 262 that restricts movement of the primary container assembly 212 in the second direction due to resistance from the tissue of the patient and/or due to a force from the resilient member 214 when deformed. Pursuant to this, the release mechanism 262 includes one or more stops 264 that extend within or through the casing 202. In a first form as shown in FIG. 7, the stops 264 extend into a path of the primary container assembly 212 and, specifically, the reservoir 216 thereof to engage the flange 246 of the reservoir 216 or housing 231 and restrict movement of the primary container assembly 212 in the second direction. In a second form as shown in FIG. 8, the stops 264 engage both the primary container assembly 212 and the resilient member 214 to hold the resilient member 214 in the same deformed state until release is desired.

In either form, the release mechanism 262 can be disengaged from the primary container assembly 212 in a first position to allow the drive mechanism 232 to drive the needle 226 to the subcutaneous location. Thereafter, the release mechanism 262 can be moved or biased to a second position corresponding to the stops 264 engaging the flange 246 or resilient member 214 or both. By one approach, the release mechanism 262 can further include arms 266 extending from the stops 264 so that a user can manipulate the release mechanism 262. As shown, the arms 266 can include a first portion 268 extending generally along the casing 202 and a second portion 270 extending outwardly from the casing 202 at an angle with respect thereto. So configured, a user can push or squeeze the second portions 270 toward the casing 202, which causes the arms 266 to pivot about the corner between the first and second portions 268, 270 to radially withdraw the stops 264 out of engagement with the reservoir 216 or resilient member 214. The pivoting point may be secured to casing 202 with a hinge or similar mechanisms that allow the pivoting movement of the arms 266. Of course, other configurations are possible. For example, a user can grasp the stop directly and pull the stop radially outwardly, or movement of the stop can be driven by a drive in response to movement of a catch or in response to actuation of a switch. If desired, the device 200 can include an interlock mechanism 272 (not shown) to prevent activation of partial needle retraction before the completion of needle insertion.

After the stops 264 are moved out of engagement with the reservoir 216 or both the primary container assembly 212 and the resilient member 214, the resilient member 214 is released to drive the primary container assembly 212 in the second direction to partially retract the needle 226. As shown in FIGS. 7 and 8, the casing 202 can include upper limit stops 274 to provide a hard stop for movement of the primary container assembly 212 in the second direction. The upper limit stops 274 can therefore ensure that the needle 226 is not retracted out of the injection cavity prior to the drug dispensing operation. Additionally, the assembly 260 may include a locking mechanism 276 to lock the needle 226 at the partially retracted position. As shown in FIG. 7, the locking mechanism 276 can include wedges 278 that are biased by springs 280 to extend into a path of the reservoir 216. So configured, the reservoir 216 engages the angled surface of the wedges 278 as the reservoir 216 is driven in the second direction and shifts the wedges 278 radially outwardly against the force of the springs 280. In the form of FIG. 7, after the flange 246 clears the wedges 278, the springs 280 drive the wedges 278 underneath the flange 246 to lock the primary container assembly 212 in place. In the form of FIG. 8, the wedges 278 can engage the reservoir 216 to compress the springs 280 prior to partial needle retraction. During partial needle retraction, after the reservoir 216 clears the wedges 278 during its movement in the second direction, the compressed springs 280 can drive the wedges 278 underneath the reservoir 216 to lock the primary container assembly 212 in the partially retracted position. Alternatively, in the form of FIG. 8, the reservoir 216 can include a distal flange 282 to lock the primary container assembly 212 in place. To securely hold the primary container assembly 212 against movement, the wedges 278 can be spaced from the upper limit stops 274 generally, i.e., 0-1 or 0-2 mm, equal to the thickness of the flange 246 in the form of FIG. 7 or generally equal to the distance between the distal flange 282 and the proximal flange 246 in the form of FIG. 8. In any of the above forms, the locking mechanism 276 can be disengaged from the primary container assembly 212 in a first position to allow the drive mechanism 232 to drive the needle 226 to the subcutaneous location. Thereafter, the locking mechanism 276 can be moved or biased to an engaged position.

Figure 9:
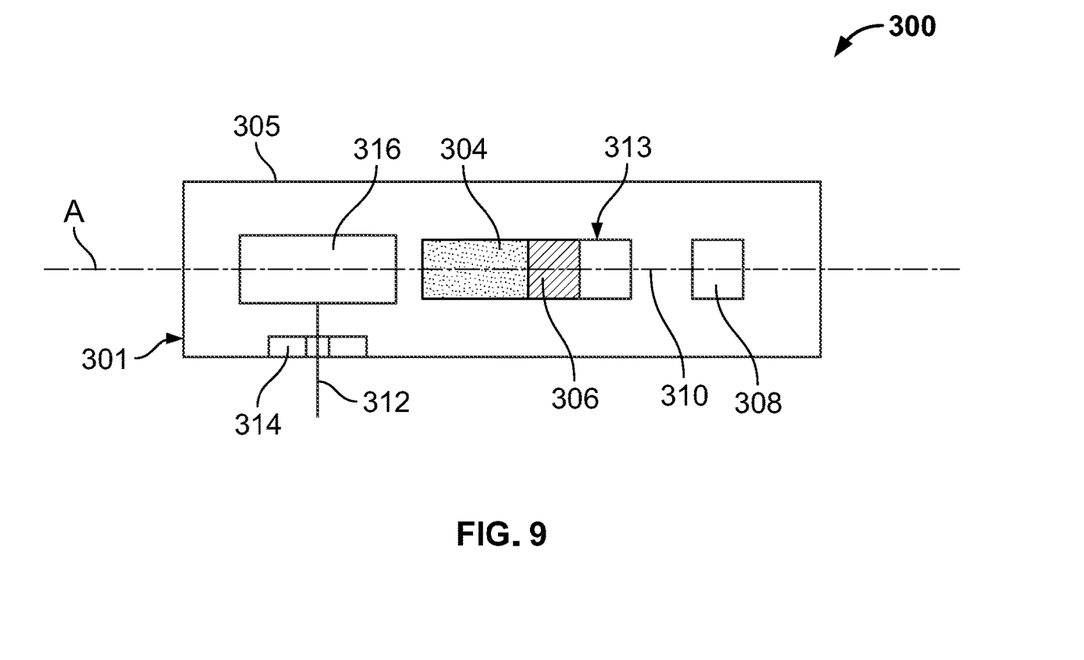
FIG. 9 is a diagrammatic view of a wearable drug delivery device in accordance with various embodiments of the present disclosure.

While the foregoing description has been relatively limited to specific drug delivery devices that resemble conventional auto-injectors, the principles of the present disclosure are equally applicable to other types of injectors such as wearable injectors, which can also be referred to as on-body injectors. For example, FIG. 9 depicts an alternative drug delivery device 300 that can include a wearable injector. Unlike the autoinjectors described above, the drug delivery device of FIG. 9 can have a generally horizontally oriented configuration with some or all drug delivery components disposed in stacked relation along a horizontal axis A within a housing 301, expect for a drug delivery member 312, which can be oriented generally perpendicular to or transverse to a skin surface of the user. Regardless, the drug delivery device 300 can include a primary container assembly 313 including at least a reservoir 302 having a drug 304 contained therein, a plunger stopper 306 disposed within the reservoir 302 and sildably movable therein along the axis A, a drive mechanism 308 coupled to a plunger rod 310 to drive the plunger stopper 306 through the reservoir 302, and a needle insertion mechanism 316 configured to insert the drug delivery member 312 to a desired subcutaneous depth within the user. In some versions, the drug delivery member 312 of the drug delivery device 300 of FIG. 9 can include a soft cannula or a rigid hollow needle. In either configuration, the needle insertion mechanism 316 is typically employed to move the drug delivery member 312 from a first position retracted inside of the housing 301 to a second position extending out of the housing 301 and inserted into the skin of the patient. If the drug delivery member 312 is a rigid hollow needle, the rigid hollow needle remains in the patient's subcutaneous tissue throughout administration of the drug. If the drug delivery member 312 is a soft cannula, the needle insert mechanism 316 can include a trocar that inserts the soft cannula. The soft cannula remains in the patient throughout drug delivery, while the trocar is retracted to open a flow path through the soft cannula.

As depicted in FIG. 9, the drug delivery device 300 further includes a resilient member 314 disposed between the outer casing 305 and the primary container assembly 313 and, more particularly, between the outer casing 305 and the needle insertion mechanism 316, which itself is disposed between the outer casing 305 and the primary container assembly 313. So configured, as the needle insertion mechanism 316 moves the drug delivery member 312 to the second position, the resilient member 314 becomes compressed such that after the drug delivery member 314 is inserted to a predetermined depth, the resilient member 314 at least partially returns to an original configuration and applied a bias force to the drug delivery member 312 to slightly retract the drug delivery member 312 from second position. This slight retraction action relieves pressure in the injection cavity in the patient. In some versions, the resilient member 314 can become compressed under a compressive load applied to the resilient member 314 by a component such as a flange, a plate, an arm, etc. of the needle insertion mechanism 316. In other versions, the resilient member 314 is compressed under force applied by a component such as a flange, plate, arm or other structure carried by the drug delivery member 312 itself. As with other embodiments described herein the resilient member 314 can include any one or more varieties of biasing member such as a spring, an elastomeric bumper, or another of the other types of resilient members described with earlier embodiments.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number 2 as set forth therein in FIG. 2 and/or the heavy chain of sequence identification number 4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers 305-351, including TN8-19-1 through TN8-19-40, TN8-19 con1 and TN8-19 con2; peptibodies of the mL2 family of sequence identification numbers 357-383; the mL15 family of sequence identification numbers 384-409; the mL17 family of sequence identification numbers 410-438; the mL20 family of sequence identification numbers 439-446; the mL21 family of sequence identification numbers 447-452; the mL24 family of sequence identification numbers 453-454; and those of sequence identification numbers 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; AbIK; AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (y4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences designated therein as, respectively, sequence identification number 1 and sequence identification number 7); 5D (having light chain variable and heavy chain variable sequences designated therein as, respectively, sequence identification number 2 and sequence identification number 9); 2H (having light chain variable and heavy chain variable sequences designated therein as, respectively, sequence identification number 3 and sequence identification number 10); 43H (having light chain variable and heavy chain variable sequences designated therein as, respectively, sequence identification number 6 and sequence identification number 14); 41H (having light chain variable and heavy chain variable sequences designated therein as, respectively, sequence identification number 5 and sequence identification number 13); and 15H (having light chain variable and heavy chain variable sequences designated therein as, respectively, sequence identification number 4 and sequence identification number 12), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number 17 and the light chain of sequence identification number 18; those having the heavy chain variable region of sequence identification number 6 and the light chain variable region of sequence identification number 8; those having the heavy chain of sequence identification number 19 and the light chain of sequence identification number 20; those having the heavy chain variable region of sequence identification number 10 and the light chain variable region of sequence identification number 12; those having the heavy chain of sequence identification number 32 and the light chain of sequence identification number 20; those having the heavy chain variable region of sequence identification number 30 and the light chain variable region of sequence identification number 12; those having the heavy chain sequence of sequence identification number 21 and the light chain sequence of sequence identification number 22; those having the heavy chain variable region of sequence identification number 14 and the light chain variable region of sequence identification number 16; those having the heavy chain of sequence identification number 21 and the light chain of sequence identification number 33; and those having the heavy chain variable region of sequence identification number 14 and the light chain variable region of sequence identification number 31, as disclosed in the foregoing publication. A specific antibody contemplated is antibody 1119 as disclosed in the foregoing U.S. publication and having a complete heavy chain of sequence identification number 17 as disclosed therein and having a complete light chain of sequence identification number 18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No.

7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number 8 and a light chain variable region having sequence identification number 6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BITE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as autoinjector drug delivery devices or other kinds of drug delivery devices, can also be utilized in other kinds of drug delivery devices, such as on-body injector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
an outer casing including one or more sidewalls, a distal end wall, and a proximal end wall defining an interior, the distal end wall having an opening extending therethrough;
a primary container assembly at least partially received within the interior of the outer casing, the primary container assembly including a reservoir having a sidewall defining an interior containing a drug to be expelled, a plunger stopper disposed within the interior of the reservoir to expel the drug therefrom, and a drug delivery member operably connected to the reservoir and configured to be fluidly coupled to the interior thereof, at least the drug delivery member being movable between first and second positions with respect to the outer casing; and
a resilient member disposed between the primary container assembly and the outer casing, wherein upon moving the drug delivery member to the second position in which the delivery member is driven through the opening and prior to the plunger stopper expelling the drug from the interior of the reservoir, the resilient member is in a deformed state that biases the drug delivery member to move in a retraction direction toward the first position to partially retract the drug delivery member to a retracted position, whereby the plunger stopper expels the drug from the interior of the reservoir while the drug delivery member is in the retracted position.

2. The drug delivery device of claim 1, wherein the primary container assembly includes a distal end, and the resilient member is disposed between the distal end of the primary container assembly and the distal end wall of the outer casing.

3. The drug delivery device of claim 2, wherein the distal end of the primary container assembly comprises a distal end of the reservoir or the primary container assembly further includes a housing at least partially receiving the reservoir and drug delivery member therein and the distal end of the primary container assembly comprises a distal end of the housing.

4. The drug delivery device of claim 1, wherein the primary container assembly includes an outwardly projecting flange at a proximal end thereof opposite the drug delivery member; the outer casing includes an inwardly projecting flange; and the resilient member is disposed between the outwardly and inwardly projecting flanges.

5. The drug delivery device of claim 4, wherein the proximal end of the primary container assembly comprises a proximal end of the reservoir.

6. The drug delivery device of claim 4, wherein the primary container assembly further includes a housing at least partially receiving the reservoir and drug delivery member therein; and the proximal end of the primary container assembly comprises a proximal end of the housing.

7. The drug delivery device of claim 1, wherein the resilient member comprises a spring or an elastomeric bumper.

8. The drug delivery device of claim 1, wherein the resilient member comprises one or more cantilevered tabs extending inwardly from the one or more sidewalls of the outer casing, the cantilevered tabs including inward end portions disposed within a path of the primary container assembly.

9. The drug delivery device of claim 1, further comprising a drive mechanism configured to drive movement of the drug delivery member with respect to the outer casing in an insertion direction from the first position to the second position such that the drug delivery member extends through the opening in the distal end wall of the outer casing for a drug delivery member insertion operation.

10. The drug delivery device of claim 9, wherein the drive mechanism further comprises a drive rod, the drive mechanism configured to drive the plunger rod to drive movement of the plunger stopper through the reservoir to expel a drug through the drug delivery member during a drug delivery operation; and the plunger stopper being driven through the reservoir causes the resilient member to deform and bias the primary container assembly to move in the second, opposite direction with respect to the outer casing to partially retract the drug delivery member after the drug delivery operation.

11. The drug delivery device of claim 1, further comprising a release member engaging the primary container assembly or both the primary container assembly and the resilient member; and wherein the resilient member is held in the deformed state by the release member.

12. The drug delivery device of claim 1, further comprising a locking mechanism including a lock member deflectable by the primary container assembly as the primary container assembly is moved in the retraction direction and a biasing mechanism configured to bias the lock member into a path of a portion of the primary container assembly in the insertion direction to restrict further movement of the primary container assembly.

\* \* \* \* \*